(12) United States Patent
Myerburg

(10) Patent No.: US 9,784,725 B2
(45) Date of Patent: Oct. 10, 2017

(54) LIGHT REFRACTION IMAGING TO MEASURE LIQUID VOLUME

(71) Applicant: University of Pittsburgh—Of the Commonwealth System of Higher Education, Pittsburgh, PA (US)

(72) Inventor: Michael Myerburg, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 15/157,475

(22) Filed: May 18, 2016

(65) Prior Publication Data

US 2016/0327540 A1 Nov. 10, 2016

(51) Int. Cl.
*G01N 33/487* (2006.01)
*G01N 21/41* (2006.01)
*G01N 21/25* (2006.01)
*G01N 21/64* (2006.01)
*G01N 33/50* (2006.01)

(52) U.S. Cl.
CPC ......... *G01N 33/487* (2013.01); *G01N 21/253* (2013.01); *G01N 21/41* (2013.01); *G01N 21/6428* (2013.01); *G01N 33/5044* (2013.01)

(58) Field of Classification Search
CPC .. G01N 21/253; G01N 21/21; G01N 21/6452; G01N 21/41; G01N 21/956; G01N 21/4788; G01N 33/487; G01N 33/5044; G01N 21/6428; G01B 11/24; G01B 11/30; G01B 9/023; G01B 11/306; G01B 11/06

See application file for complete search history.

(56) References Cited

U.S. PATENT DOCUMENTS

| | | | |
|---|---|---|---|
| 5,753,203 A | 5/1998 | Goodwin et al. | |
| 6,097,831 A * | 8/2000 | Wieck | G01N 33/54366 382/128 |
| 6,743,576 B1 | 6/2004 | Sabry et al. | |

(Continued)

OTHER PUBLICATIONS

Resonant Scanning in Laser Confocal Microscopy by Larson et al. (https://www.microscopyu.com/articles/confocal/resonantscanning.html).

(Continued)

*Primary Examiner* — Tarifur Chowdhury
*Assistant Examiner* — Mohamed K Amara
(74) *Attorney, Agent, or Firm* — The Webb Law Firm

(57) ABSTRACT

A method to measure the volume of fluid present that relies on the pattern of light refraction as it passes though an airway surface liquid (ASL) meniscus. The method comprises allowing epithelial cells to grow on a membrane in a well so as to form a fluid meniscus about the perimeter of the well. The well is then illuminated by a light source. The illuminated cells in the well are then optically imaged by a scanner, a flat bed optical scanner, a camera, or any device capable of imaging. Microscopy may be used but is not needed, and high powered microscopy is certainly not needed. Then the imaging information from the cells in the well is used to determine a property of the meniscus in the well. Specifically, the imaging information can be analyzed to determine the dimensions, shape, and/or volume of the meniscus and the fluid in the well.

20 Claims, 9 Drawing Sheets

(56) References Cited

U.S. PATENT DOCUMENTS

| | | | |
|---|---|---|---|
| 7,224,470 B2* | 5/2007 | Vaux | G01N 13/02 |
| | | | 356/237.2 |
| 8,448,510 B2* | 5/2013 | Scheiner | G01F 23/292 |
| | | | 73/290 R |
| 2007/0171417 A1 | 7/2007 | Cromwell et al. | |
| 2007/0258043 A1* | 11/2007 | Suzuki | A61B 3/101 |
| | | | 351/205 |
| 2009/0041855 A1* | 2/2009 | Hibino | A61K 9/0048 |
| | | | 424/583 |
| 2010/0330061 A1 | 12/2010 | Conner | |
| 2011/0067490 A1 | 3/2011 | Walsh et al. | |
| 2011/0134723 A1* | 6/2011 | Stearns | G01F 23/296 |
| | | | 367/99 |
| 2012/0126689 A1 | 5/2012 | Gaerditz et al. | |
| 2013/0050851 A1* | 2/2013 | Machida | B29D 11/00269 |
| | | | 359/742 |
| 2013/0288964 A1 | 10/2013 | Bolscher et al. | |
| 2016/0338585 A1* | 11/2016 | Arieli | G01B 9/02025 |

OTHER PUBLICATIONS

Abramoff et al., Image Processing with ImageJ, Biophotonics International, 2004, 7 pages.

Coakley et al., "17beta-Estradiol inhibits Ca2+-dependent homeostasis of airway surface liquid volume in human cystic fibrosis airway epithelia", The Journal of Clinical Investigation, 2008, 4025-4035, vol. 118, No. 12.

Coote et al., "Camostat Attenuates Airway Epithelial Sodium Channel Function in Vivo through the Inhibition of a Channel-Activating Protease", The Journal of Pharmacology and Experimental Therapeutics, 2009, 764-774, vol. 329, No. 2.

Deterding et al., "Safety and Tolerability of Denufosol Terasodium Inhalation Solution, a Novel P2Y2 Receptor Agonsit: Results of a Phase 1/Phase 2 Multicenter Study in Mild to Moderate Cystic Fibrosis", Pediatric Pulmonology, 2005, 339-348, vol. 39.

Deterding et al., "Phase 2 Randomized Safety and Efficacy Trial of Nebulized Denufosol Tetrasodium in Cystic Fibrosis", Am. J. Respir. Crit. Care Med., 2007, 362-369, vol. 176.

Devor et al., "UTP inhibits Na+ absorption in wild-type and DeltaF508 CFTR-expressing human bronchial epithelia", The American Physiological Society, 1999, 827-836.

Donaldson et al., "Mucus Clearance and Lung Function in Cystic Fibrosis and Hypertonic Saline", The New England Journal of Medicine, 2009, 241-250, vol. 354, No. 3.

Elkins et al., "A Controlled Trial of Long-Term Inhaled Hypertonic Saline in Patents with Cystic Fibrosis", The New England Journal of Medicine, 2006, 229-240, vol. 354, No. 3.

Goralski et al., "Osmolytes and ion transport modulators: new strategies for airway surface rehydration", Current Opinion in Pharmacology, 2010, 294-299, vol. 10.

Hamosh et al., "Correlation Between Genotype and Phenotype in Patents with Cystic Fibrosis", The New England Journal of Medicine, 2014, 1308-1313, vol. 329, No. 18.

Harvey et al., "Measurement of the Airway Surface Liquid Volume with Simple Light Refraction Microscopy", Am. J. Respir. Cell. Mod. Biol. 2011, 592-599, vol. 45.

Hirsh et al., "Evaluation of Second Generation Amiloride Analogs as Therapy for Cystic Fibrosis Lung Disease", The Journal of Pharmacology and Experimental Therapeutics, 2004, 929-928, vol. 311, No. 3.

Hirsh et al., "Pharmacological Properties of N-(3,5-Diamino-6-chloropyrazine-2-carbonyl)-N'-4[4-(2,3-dihydroxypropoxy)phenyl]butyl-guanidine Methanesulfonate (552-02), a Novel Epithelial Sodium Channel Blocker with Potential Clinical Efficacy for Cystic Fibrosis Lung Disease", The Journal of Pharmacology and Experimental Therapeutics, 2008, 77-88, vol. 325, No. 1.

Hutt et al., "Reduced Histone Deacetylase 7 Activity Restores Function to Misfolded CFTR in Cystic Fibrosis", Nat. Chem. Biol., 2010, 1-24, vol. 6, No. 1.

Jaques et al., "Inhaled Mannitol Improves Lung Function in Cystic Fibrosis", Chest, 2008, 1388-1396, vol. 133, No. 6.

Jiang et al., "Altered Fluid Transport Across Airway Epithelium in Cystic Fibrosis", Science, 1993, 424-427, vol. 262.

Knowles et al., "Increased Bioelectric Potential Difference Across Respiratory Epithelia in Cystic Fibrosis", The New England Journal of Medicine, 1987, 1489-1495, vol. 305, No. 25.

Knowles et al., "Mucus Clearance as a primary innate defense mechanism for mammalian airways", The Journal of Clinical Investigation, 2002, 571-577, vol. 109, No. 5.

Mall et al., "Increased airway epithelial Na+ absorption produces cystic fibrosis-like lung disease in mice", Nature Medicine, 2004, 487-493, vol. 10, No. 5.

Matsui et al., "Osmotic water permeabilities of cultured, well-differentiated normal and cystic fibrosis airway epithelia" The Journal of Clinical Investigation, 2000, 1419-1427, vol. 105, No. 10.

Matsui et al., "Evidence for Periciliary Liquid Layer Depletion, Not Abnormal Ion Composition, in the Pathogenesis of Cystic Fibrosis Airways Disease", Cell, 1998, 1005-1015, vol. 95.

Matsui et al., "Coordinated Clearance of Periciliary Liquid and Mucus from Airway Surface", The Journal of Clinical Investigation, 1998, 1125-1131, vol. 102, No. 6.

Minasian et al., "Comparison of inhaled mannitol, daily rhDNase and a combination of both in children with cystic fibrosis: a randomised trial", Thorax, 2010, 51-56, vol. 65.

Myerburg et al., "Airway Surface Liquid Volume Regulates ENaC by Altering the Serine Protease-Protease Inhibitor Balance", The Journal of Biological Chemistry, 2006, 27942-27949, vol. 281, No. 38.

Myerburg et al., "Development of a Simple Method to Measure ASL Volume", Pediatric Pulmonology, 2009, 2 pages.

Myerburg et al., "Acute Regulation of the Ephithelial Sodium Channell Airway Epithelia by Proteases and Trafficking", Am. J. Respir. Cell Mol. Biol., 2010, 712-719, vol. 43.

Rowe et al., "DeltaF508 CFTR processing correction and activity in polarized airway and non-airway cell monolayers", Pulm. Pharmacol. Ther. 2010, 268-278, vol. 23, No. 4.

Singh et al., "Stimulation of Cl(−) Secretion by Chlorzoxazone1", The Journal of Pharmacology and Experimental Therapeutics, 2000, 778-787, vol. 292, No. 2.

Stuurman et al., "Manager: Open Source Software for Light Microscope Imaging", Microscopy Today, 2007, 41-43, vol. 15, No. 3.

Tarran et al., "Normal and Cystic Fibrosis Airway Surface Liquid Homeostasis", The Journal of Biological Chemistry, 2005, 35751-35759, vol. 280, No. 42.

Tarran et al., "The Relative Roles of Passive Surface Forces and Active Ion Transport in the Modulation of Airway Surface Liquid Volume and Composition", J. Gen. Physiol, 2001, 223-236, vol. 118.

Tarran et al., "The CF Salt Controversy: In Vivo Observations and Therapeutic Approaches", Molecular Cell, 2001, 149-158, vol. 8.

Tarran et al., "Soluble Mediators, Not Cilia, Determine Airway Surface Liquid Volume in Normal and Cystic Fibrosis Superficial Airway Epithelia", J. Gen. Physiol., 2006, 591-604, vol. 127, No. 5.

Traynor-Kaplan et al., "INO-4995 Therapeutic Efficacy Is Enhanced with Repeat Dosing in Cystic Fibrosis Knockout Mice and Human Epithelia", Am. J. Respir. Cell Mod. Biol. 2010, 105-112, vol. 42.

Goor et al., "Rescue of CF airway epithelial cell function in vitro by CFTR potentiator, VX-770" PNAS, 2009, 18825-18830, vol. 106, No. 44.

Zhou et al., "Preventive but Not Late Amiloride Therapy Reduces Morbidity and Mortality of Lung Disease in betaENaC-overexpressing Mice", Am J. Respir. Crit. Care Med., 2008, 1245-1256, vol. 178.

Zhu et al., "The SERPINE2 Gene Is Associated with Chronic Obstructive Pulmonary Disease in Two Large Populations", Am. J. Respir. Crit. Care Med., 2007, 167-173, vol. 176.

\* cited by examiner

LIGHT REFRACTION IMAGING TO MEASURE LIQUID VOLUME

STATEMENT REGARDING FEDERALLY SPONSORED RESEARCH AND DEVELOPMENT

This invention was made with government support under Grant Nos. K08 HL087932 and P30 DK072506, awarded by the National Institutes of Health. The government has certain rights in the invention.

CROSS REFERENCE TO RELATED APPLICATIONS

This application is a continuation of U.S. patent application Ser. No. 13/650,198, filed Oct. 12, 2012, which claims the benefit of U.S. Provisional Application No. 61/547,106, filed Oct. 14, 2011, entitled "Light Refraction Imaging to Measure Liquid Volume," each of which is incorporated herein by reference in its entirety.

Provided herein are methods and systems for measurement of liquid volumes, e.g., surface hydration, in an air-liquid cell culture, including uses of the method for determining an effect of a drug composition on the surface hydration.

Airway surface dehydration impairs mucus clearance from the lung and is involved in the pathogenesis of cystic fibrosis (CF). Accordingly, numerous therapeutics have been developed to restore mucosal hydration to the CF airway, yet preclinical evaluation of these agents is hindered by the paucity of methods available to directly measure the airway surface liquid (ASL) volume.

Mucociliary clearance, the primary innate defense mechanism of the conducting airways, is strongly influenced by the hydration state of the airway lumen. In cystic fibrosis (CF) lung disease, the clearance of mucus and inhaled pathogens is impaired due to an inadequate volume of airway surface liquid (ASL), resulting in mucus obstruction and chronic airway infection. Therefore, over the last decade a plethora of therapeutic agents have been developed to block Na absorption augment Cl⁻ secretion, or osmotically expand the ASL volume in an effort to restore proper hydration to the airway surface. Well-differentiated primary human bronchial epithelial (HBE) cultures have provided an excellent model to study the physiological processes that underlie mucosal hydration and investigate the effects of therapeutic agents. However, standardized methods to directly study the effects of these compounds on the ASL are lacking.

Airway epithelia are relatively permeable to water and therefore fluid flux across the airway is believed to be driven by osmotic gradients established by active ion transport. In non-CF epithelia, $Na^+$ absorption through ENaC increases under conditions when the ASL volume is high and ASL absorption increases accordingly. Conversely, when the ASL volume is depleted, $Na^+$ absorption is inhibited and $Cl^-$ secretion increases; allowing for net secretion of ASL to maintain mucosal hydration. Whereas this dynamic system maintains an optimal ASL volume in healthy HBE, airway epithelia from CF patients have an impaired ability to secrete $Cl^-$, due to mutant CFTR, and display unregulated Na absorption though ENaC; this leads to excessive ASL absorption and mucosal dehydration. Based on these properties, it is believed that the changes in the short circuit current (Isc) across HBE predict changes in airway surface hydration. However, there are several factors that may limit the ability of Isc to predict changes in the ASL volume.

Using chambers are used to measure short-circuit current as an indicator of ion transport across an epithelium. Using chamber measurements are performed with extremely large fixed volumes of fluid and pharmacological agents, relative to what is normally experienced by the airways. Due to these non-physiological conditions, Isc measurements do not take into account (i) the effects of soluble endogenous regulators of airway ion transport/ASL flux and (ii) the ability of the airways to spontaneously remove/metabolize pharmacological compounds that have been added to the mucosal surface. Therefore, a drug/therapy may not have the same effect in-vivo that what was observed in the Using chamber. Additionally, Isc measurements fail to account for changes in paracellular permeability and the potential contribution of non-electrogenic ion transport. Therefore, ASL is better measured directly to understand the effects of therapeutic agents on mucosal hydration.

The ASL height can be directly measured using confocal microscopy. In these assays, a small bolus of fluid, containing a non-absorbable fluorescently labeled dextran is applied to the apical surface of HBE cultures and then the height of this liquid layer is serially measured over time. ASL height measurements have provided a direct means to investigate ASL regulation and have dramatically increased our knowledge of basic CF pathophysiology. However, these methods require sophisticated equipment and can only be performed in specialized labs with experience performing this technique.

Accordingly there is a need for a simple, rapid methodology to measure the ASL volume using readily available resources.

SUMMARY

Provided herein are methods for measuring a volume of fluid present in an cell culture that relies on a pattern of light refraction as it passes through an ASL meniscus. The method in several embodiments comprises allowing epithelial cells to grow on a membrane in a well in an air-liquid culture so as to form a fluid meniscus about the perimeter of the well. Then the well is then illuminated by a light source, for example natural light, artificial light, ultraviolet (UV) light, polarized light, non-polarized light, coherent light, non-coherent light, diffused light, etc. The illuminated cells in the well are then optically imaged by a scanner, a flat bed optical scanner, a camera, or any device capable of imaging. Microscopy may be used but is not needed, and high powered microscopy is certainly not needed. Then the imaging information from the cells in the well is used to determine a property of the meniscus in the well. Specifically, the imaging information can be analyzed to determine the dimensions, shape, and/or volume of the meniscus and the fluid in the well.

Compared to traditional methods of assessing the ASL, the present method is simple to perform, does not require sophisticated equipment, and can be readily standardized as a uniform measure of mucosal hydration. Furthermore, it is suitable to high throughput screening assays that could be used to screen the novel therapeutics being developed for airway disease. The methods and devices described herein are rapid, use inexpensive equipment, are suitable for high throughput assays and are standardized and objective. The methods described below where developed at least in part in a study described in "Measurement of the Airway Surface Liquid Volume with Simple Light Refraction Microscopy", Am J Respir Cell Mol Biol. 2011 September; 45(3): 592-599, which is incorporated herein by reference in its entirety.

In one embodiment, a method of quantifying surface hydration in an air-liquid culture of epithelial cells on a membrane is provided. The method comprises: culturing epithelial cells in an air-liquid culture on a membrane in a well, the well comprising a membrane and a wall about a perimeter of the membrane, the membrane contacting cell culture medium on a side opposite the cells; illuminating the well in a manner such that a volume of a meniscus of liquid on the cells, if present, can be determined from an aspect of light in the well; imaging the well, thereby producing an image of the well; producing, using a computer-implemented method, a profile of the one aspect of light in an area of the well adjacent to the wall and extending past a portion of the wall in which a meniscus forms when a liquid is present on the cells, calculating, using a computer-implemented method, a volume of liquid in the meniscus using the profile of the aspect of light as representative of a total volume of liquid present on the cells, thereby determining a measurement of the volume of liquid on the cultured epithelial cells in the well; and providing an output from calculating step of the volume of liquid on the cultured epithelial cells in the well.

In another embodiment, a method of determining an ability of a composition to affect surface hydration of epithelial cells is provided. The method comprises: culturing epithelial cells in two or more air-liquid cultures on two or more membranes in two or more wells of a cell culture device comprising two or more wells, each well independently comprising a membrane and a wall about a perimeter of the membrane and each membrane contacting cell culture medium on a side opposite the cell; administering a composition to at least one of the two or more cell cultures and administering either a different composition, different amounts of the same composition or nothing to one or more different cell cultures of the two or more cell cultures; illuminating the wells comprising the two or more cell cultures in a manner such that a volume of a meniscus of liquid on the cells, if present, can be determined from an aspect of light in the wells; imaging the two or more wells at the same time, thereby producing an image of the wells, producing for each of the two or more wells, using a computer-implemented method, a profile of the aspect of light in an area of the wells adjacent to the wall of each well and extending past a portion of the walls in which a meniscus forms when a liquid is present on the cells; calculating, using a computer-implemented method, a volume of liquid in the meniscus of each of the cell cultures using the profile of the one aspect of light as representative of a total volume of liquid present on the cells; and producing an output from calculating step of the volume of liquid on the cultured epithelial cells in each of the two or more wells.

In embodiments of either of the aforementioned methods, according to one embodiment, various embodiments, the well is illuminated by light from an opposite side of the membrane from an imaging device used for imaging the well such that light is refracted differently at a meniscus adjacent the wall as compared to a point on the membrane where no meniscus forms. The light may be transmitted light or ultraviolet light if the ASL is labeled with a fluorescent probe. The aspect of the light is any measurable physical property of the light that may be quantified by imaging in either the visual or non-visual spectrum, such as, for example and without limitation light intensity or color. According to one embodiment, the image is a grayscale image of the well and the aspect of light in the well is gray level. The image may be taken by any suitable imaging device, such as a flat bed optical scanner, an optical plate reader or a top-illumination scanner. Because the methods do not require a microscopic image, the image is taken with an imaging device (camera) that either does not magnify the image optically or the optical magnification is low, such as less than 40× or from 0.5× to 4×.

The methods and, independently, steps thereof, where possible, are typically computer-implemented, that is by software (executable instructions) processed by a processor. According to one method, an area under the curve (AUC) is calculated for the profile when the volume of the volume of liquid in the meniscus is calculated. In one embodiment, the profile is taken across the meniscus on a line extending perpendicular from the wall. The methods may employ a device comprising two or more discrete cell cultures at independently addressable physical locations, such as an array or multi-well dishes, for example as are known in the art and are commercially available. In a multiwall device, the cells are cultured on one or more membranes of a cell culture device with two or more wells, each well independently comprising a membrane and a wall about a perimeter of the membrane and each membrane contacting cell culture medium on a side opposite the cells. To facilitate comparison between two sample cultures, cells can be cultured on two or more membranes in two or more wells of the device and the two or more wells are imaged at the same time and volumes of liquid in each of the two or more wells is determined and output for each of the two or more wells according to steps (d)-(f). For example a test sample is placed in one well and a second well can be used as a control. According to one embodiment, for example useful in cystic fibrosis—related assays, the cells are bronchial airway cells.

According to an alternate embodiment, the methods further include adding an optically-active composition to the ASL liquid prior to imaging. The optically-active compositions affect some property of the ASL such that the meniscus can be images in a manner that permits quantification of the meniscus volume according to methods described herein. Suitable optically-active compositions include, without limitation: particles that suspend in the ASL that affect the passage of light through the ALS in a detectable manner, including opaque particles or light-scattering particles such as gold particles, latex particles, polymeric particles, emulsions, etc.; non-absorbable dyes or fluorescent compositions, such as non-absorbable fluorescently labeled dextran.

Also provided is a system for implementing the methods described above in any of the described embodiments. The system comprises an imaging device; and a computer connected to the imaging device comprising a processor and executable instructions for quantifying surface hydration in an air-liquid culture of epithelial cells on a membrane from an image of an air-liquid culture on a membrane in a well, the well comprising a wall about a perimeter of the well, in which the image is generated by illuminating the well in a manner such that a volume of a meniscus of liquid on the cells, if present, can be determined from an aspect of light in the well, the executable instructions, when processed by the computer: producing a profile of the one aspect of light in an area of the well adjacent to the wall and extending past a portion of the wall in which a meniscus forms when a liquid is present on the cells; calculating a volume of liquid in the meniscus using the profile of the aspect of light as representative of a total volume of liquid present on the cells, thereby determining a measurement of the volume of liquid on the cultured epithelial cells in the well; and producing an output from calculating step (ii) of the volume of liquid on the cultured epithelial cells in the well.

Further details and advantages of the invention will become clear from the following detailed description when read in conjunction with the accompanying figures.

DETAILED DESCRIPTION

Figure 1A:
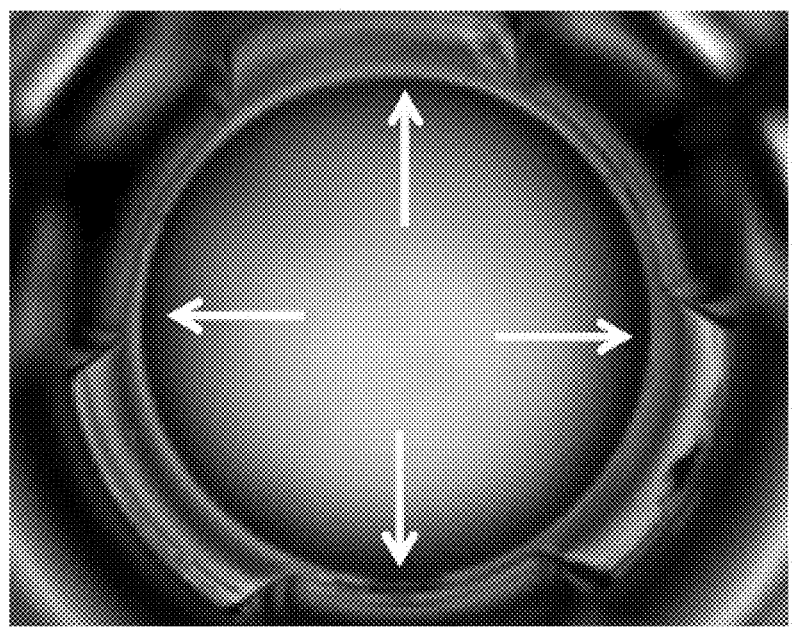
FIG. 1A are low-power images depicting the fluid meniscus that surrounds primary HBE cultures (top) and then after aspiration of the airway surface liquid (ASL) and mucus, showing that the fluid meniscus is no longer present (bottom).
Figure 1A:
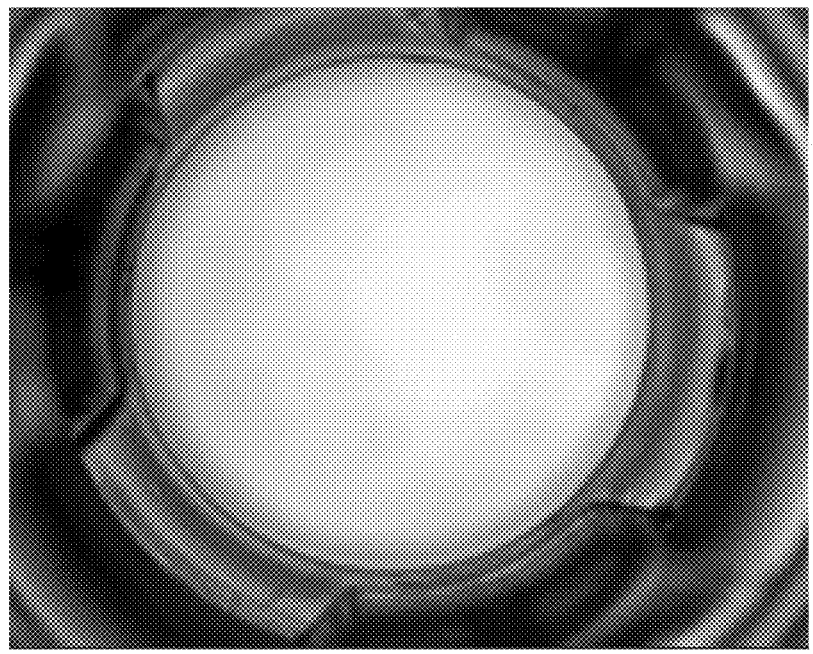

For purposes of the description hereinafter, the words "upper", "lower", "right", "left", "vertical", "horizontal", "top", "bottom", "lateral", "longitudinal", and like spatial terms, if used, shall relate to the described embodiments as oriented in the drawing figures. Unless indicated otherwise, spatial orientation is used in relation to depictions of the embodiment only for ease of description and the described embodiments are not intended to have any specific spatial orientation, other than the respective position of elements of the embodiment in relation to each-other. It is to be understood that many alternative variations and embodiments may be assumed except where expressly specified to the contrary. It is also to be understood that the specific devices and embodiments illustrated in the accompanying drawings and described herein are non-limiting exemplary embodiments of the invention.

Figure 1B:
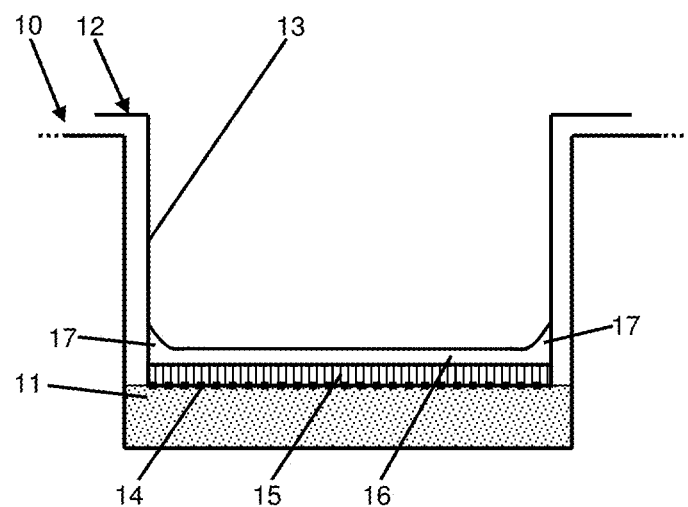
FIG. 1B is a schematic representation of a side view of the low-power images depicting a fluid meniscus that surrounds primary HBE cultures (top) and then after aspiration of the airway surface liquid (ASL) and mucus, the fluid meniscus is no longer present (bottom), as shown in FIG. 1A.
Figure 1B:
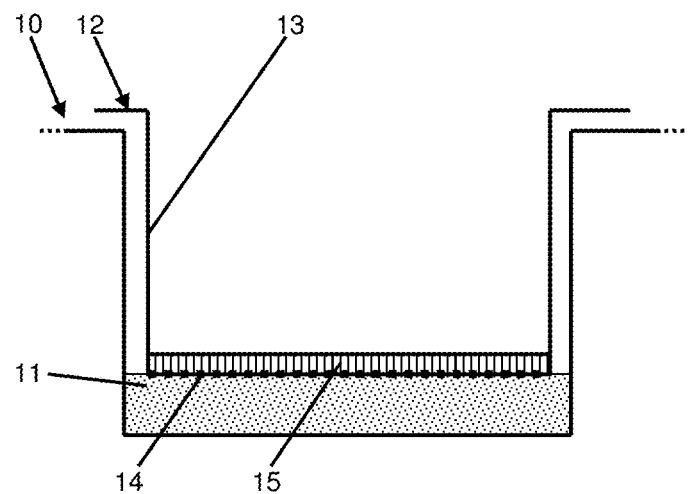

An air-liquid culture is a culture of cells on a membrane such as a filter, a hydrogel or other porous structure, in which one side of the cultured cells is exposed to air or a gas or mixture of gases, such as air supplemented with $CO_2$ and the other side of the cultured cells adjacent to the membrane is exposed to cell culture medium that permeates the membrane to the extent permitted by the membrane. Air-liquid culture devices are broadly known and available commercially. FIGS. 1A-1D depict an air-liquid culture of primary HBE cells in a typical cell culture insert, such as a Transwell® device, in which a cell culture insert is nested in a well of a cell culture container, the insert having a porous (e.g., membrane or filter) bottom and an insert wall. It should be noted that the depicted well of the cell culture container is merely exemplary and the cell culture insert may be immersed in a container in which multiple such inserts or an insert with an array of two or more insert wells contacts the same reservoir of cell culture media. At least the porous bottom of the filter insert is inserted into the well in contact with cell culture medium and cells are deposited within the insert on the porous bottom (e.g., filter) of the insert. Referring to FIGS. 1A and 1B, primary HBE cells cultured at an air-liquid interface (ALI) typically develop a liquid meniscus at the edge of a culture insert. FIG. 1A, as illustrated schematically in a side view in FIG. 1B for convenience of illustration, shows a low-power image depicting cells cultured in a cell culture well 10 comprising cell culture medium 11 (top). A Transwell® insert 12 is inserted into the well 10, forming a second well within the well 10. The insert 12 has a wall 13 and a filter bottom 14 (also referred to as a membrane) upon which a layer of HBE cells 15 is cultured. The wall 13 of the insert 12 is typically cylindrical and (substantially) perpendicular to the filter bottom or membrane 14. In the embodiment shown, Airway surface liquid (ASL) 16 is present on the cell layer 15, with a fluid meniscus 17 adjacent to the wall 13 of the insert 12. It should be noted that the amount of liquid may vary substantially or the liquid may not be present, hence the need for the quantification methods described herein. After aspiration of the ASL 16 and mucus from the cell layer 15 FIGS. 1A and 1B (bottom), the fluid meniscus 17 is no longer present. It was hypothesized that the size of the fluid meniscus might be used to determine the ASL volume and the meniscus size could be measured as an index of the epithelial surface hydration status. To establish the relationship between the meniscus and the ASL volume, a series of experiments were performed using primary HBE cultured on an air liquid interface. In the example described below the meniscus is first directly imaged using XZ confocal imaging and established the relationship between the ASL volume, ASL height, and size of the meniscus. Then, the meniscus was measured using imaging as described herein, and the two where compared to confirm the relationship between the ASL volume, ASL height, and size of the meniscus.

Figure 1C:
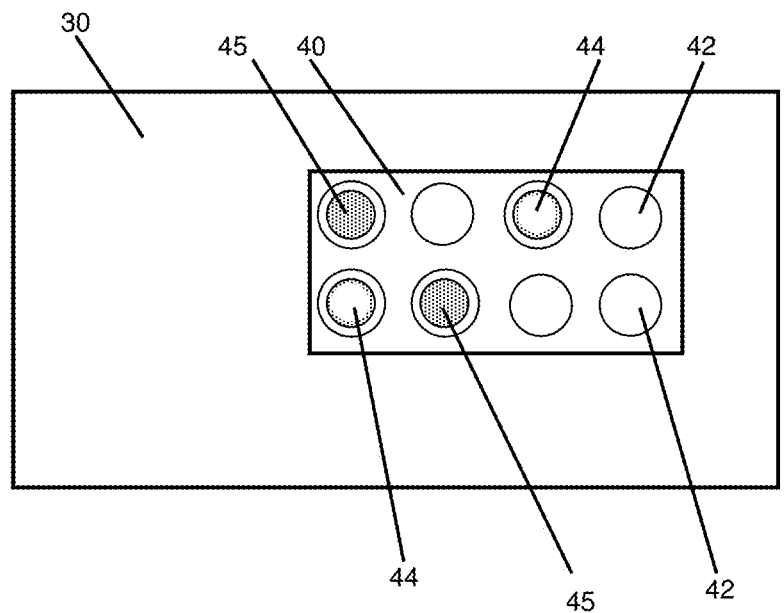
FIGS. 1C-1E are schematic diagrams of apparatus that may be used to practice methods described herein.
Figure 1D:
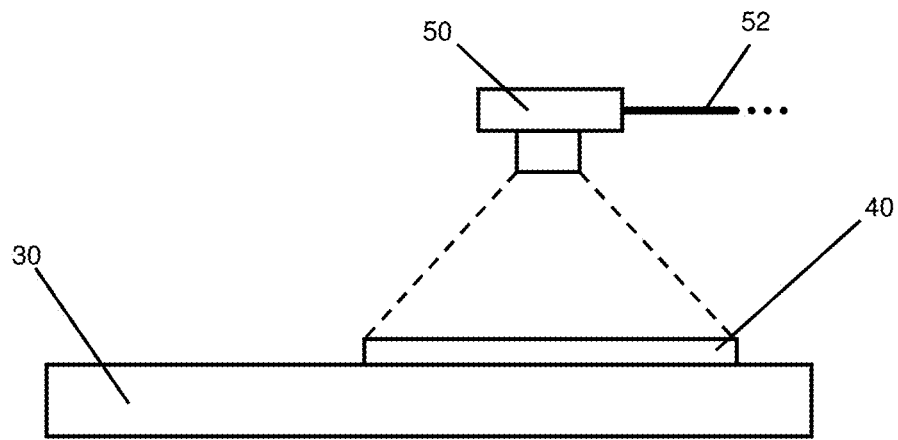

Referring to FIG. 1C, which is a schematic of an apparatus that may be used to practice the method described herein. A light source (e.g., light box) 30 is depicted, onto which multi-well plate 40 is positioned. The multi-well plate comprises wells, half of which are empty 42, and half of which are populated with inserts 44 and 45 containing cells and configured essentially as depicted in FIG. 1B. Certain inserts 44 comprise fluid and a meniscus, while other inserts 45 lack enough fluid to produce a meniscus. FIG. 1D depicts a side view of the device of FIG. 1C, showing light source 30, plate 40 and a camera 50 with and image sensor, such as, without limitation, a charge-coupled device (CCD) or complementary metal-oxide-semiconductor (CMOS) image sensor connected to a computer by a wire 52. Before sending image data to the wire or any communication interface, the data signal is optionally processed into a digital signal by any analog/digital (A/D) software and/or hardware device as are broadly known and available. Alternately, a signal from the camera 50 can be transferred to an external processing unit.

Wire 52 is depicted only as an example of a data connection, which can be wired or wireless. The data connection can be any acceptable wired or wireless computer communication device and method. If wired, the wire can be any electrical and optical data communication and follow any acceptable protocol, including, without limitation: serial, parallel USB (e.g., 2.0 or 3.0), Ethernet (e.g., IEEE 802.3 et seq. protocols), Firewire (e.g., IEEE 1394), Thunderbolt, etc. protocols, standards, connectors and interfaces. Wireless interfaces include any acceptable analog or digital communications interface, including, without limitation: 802.11 et seq. standards, such as 802.11b, g or n standards; infrared; radio frequency (RF), Bluetooth, etc. protocols, standards, connectors and interfaces.

Camera 50 optionally magnifies the image, and may comprise a microscope or other lens combinations useful in magnifying images, and magnification can be optical and/or digital (that is, software—implemented). Of note, the image may be a complete static image, as in the case of a photograph image, or any other suitable image, such as a scan of the wells, as in the case of a video image, such as an interlaced image, and in any scanning pattern.

Figure 1E:
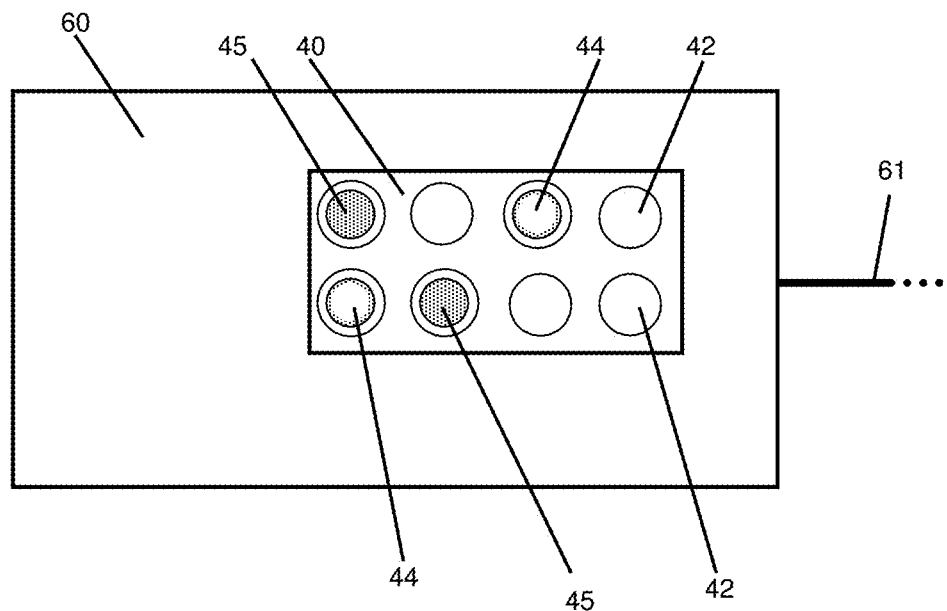

An alternate embodiment is depicted schematically in FIG. 1E in which a scanner 60, e.g., an optical plate reader of a top-illumination scanner, is used to image the plate 40. Wire 61 is used as a data connector, but as with the device of FIG. 1D, the communication interface can be any acceptable wired or wireless interface, for example, as described above. The devices of FIGS. 1D and 1E form part of an imaging system that obtains an image of the wells of a plate and analyzes the image to determine the presence and extent of a meniscus in a well of the plate. In use, the devices of FIGS. 1D and 1E obtain an image of the wells in the plate that is processed in a computer to determine a volume of a meniscus in inserts, e.g., 44 and 45 in FIGS. 1D and 1E.

A significant advantage of the devices of FIGS. 1D and 1E, is that no magnification is necessary to obtain the images and analyze them. A significant limitation of the use of microscopy to obtain images for determining meniscus volume is the expense of the microscope and the level of skill or complexity of the system necessary to implement the methods herein. In contrast, the lack of need for magnification permits obtaining an image (e.g., a non-microscopic image, such as a 1× image, a 1× to 10×, or a low numerical aperture (low NA) objective, preferably non-phase contrast, that permits imaging of an entire insert well (e.g., 0.5× to 10× and preferably 0.5× to 4× or, in terms of NA, less than 0.25 and preferably less than 0.1 for a plan achromat aperture or an equivalent thereof, preferably in combination with unfocused transmitted light when a microscope objective is used in order to reduce artifact introduced from culture structure or cells) from a scanner or rudimentary camera and analyzing that image using a computer-implemented method in a computer. A computer-implemented method is a method in which one or more steps, or all steps, are performed by a computer, and as such, any method step in a computer-implemented method described herein is performed in a computer.

A computer comprises at a minimum a processor that implements instructions. Computer architecture is extremely varied, and portions of the computer may be housed within the computer, or distributed in two or more devices. In one non-limiting example, a scanner obtains an image, converts the image to a digital representation and transmits (communicates) the digital image to a personal computer or smart device that comprises a processor, memory (e.g., RAM and caches), storage (e.g., ROM, hard drives and solid state drives (SSDs) that can be internal to the computer or in a separate device, such as an external USB 3.0 or Thunderbolt hard drive or SSD), and a display or display adaptor for displaying output from the computer. A computer also includes software, including an operating system (e.g., Windows, LINUX, Mac OS, variations thereof, etc.) and software for implementing methods such as data analysis and output, and which comprises, for example and without limitation, instructions, code, data, processes, algorithms, etc. for implementing a method. A person of ordinary skill in the engineering arts would readily envision variations of the computer as is described herein.

In use, an image of a well insert is analyzed to determine a profile of a meniscus in the image. As described below, light traveling through the meniscus and light intensity changes with the angle of the meniscus. As such, a profile of the meniscus based on light intensity can be compared to a stored profile of one or more calibration samples, or an algorithm or other process representative of light intensity changes in a meniscus in relation to volume of the meniscus, to generate a meniscus volume and/or a volume of fluid (e.g., ASL fluid) in the insert. According to one embodiment, an image, for example a grayscale image, of a well insert is obtained and is analyzed in a computer by a computer-implemented method. The process flow of the software includes obtaining a profile of the light intensity of the image in a radial line that is normal or perpendicular to (including substantially normal or perpendicular to) a wall of the well insert and calculating a volume of the meniscus based on the profile of the light intensity. The profile of light intensity may be obtained from a grayscale image and gray levels along the radial line, e.g., as described below. As would be recognized by one of ordinary skill, the methods and devices include or are in reference to well inserts that have a cylindrical wall that is perpendicular to the filter, as are commonly available commercially. Other insert shapes and configurations may be used, so long as the meniscus can be imaged and the meniscus profile is representative of the volume of liquid in the insert.

According to a first embodiment, a method of quantifying surface hydration in an air-liquid culture of epithelial cells on a membrane is provided. The method comprises: culturing epithelial cells in an air-liquid culture on a membrane in a well, the well comprising a membrane and a wall about a perimeter of the membrane, the membrane contacting cell culture medium on a side opposite the cells; illuminating the well in a manner such that a volume of a meniscus of liquid on the cells, if present, can be determined from an aspect of light (e.g., intensity or color) in the well; imaging the well, thereby producing an image of the well; producing, using a computer-implemented method, a profile of the one aspect of light in an area of the well adjacent to the wall and extending past a portion of the wall in which a meniscus forms when a liquid is present on the cells, calculating, using a computer-implemented method, a volume of liquid in the meniscus using the profile of the aspect of light as representative of a total volume of liquid present on the cells, thereby determining a measurement of the volume of liquid on the cultured epithelial cells in the well; and providing an output from calculating step of the volume of liquid on the cultured epithelial cells in the well.

According to a second embodiment, also provided is a method of determining an ability of a composition to affect surface hydration of epithelial cells. The method comprises: culturing epithelial cells in two or more air-liquid cultures on two or more membranes in two or more wells of a cell culture device comprising two or more wells, each well independently comprising a membrane and a wall about a perimeter of the membrane and each membrane contacting cell culture medium on a side opposite the cell; administering a composition to at least one of the two or more cell cultures and administering either a different composition, different amounts of the same composition or nothing to one or more different cell cultures of the two or more cell cultures; illuminating the wells comprising the two or more cell cultures in a manner such that a volume of a meniscus of liquid on the cells, if present, can be determined from an aspect of light in the wells; imaging the two or more wells at the same time, thereby producing an image of the wells, producing for each of the two or more wells, using a computer-implemented method, a profile of the aspect of light in an area of the wells adjacent to the wall of each well and extending past a portion of the walls in which a meniscus forms when a liquid is present on the cells; calculating, using a computer-implemented method, a volume of liquid in the meniscus of each of the cell cultures using the profile of the one aspect of light as representative of a total volume of liquid present on the cells; and producing an output from calculating step of the volume of liquid on the cultured epithelial cells in each of the two or more wells.

In embodiments of either of the aforementioned methods, according to one embodiment, various embodiments, the well is illuminated by light from an opposite side of the membrane from an imaging device used for imaging the well such that light is refracted differently at a meniscus adjacent the wall as compared to a point on the membrane where no meniscus forms. In all embodiments of the methods and systems described herein, the light for illuminating the wells may be transmitted light that is passed through the cell culture or illumination from the same side as the imaging device, and may be coherent (e.g., laser), or non-coherent (e.g., a light bulb) and any suitable wavelength. The aspect of the light is any measurable physical property of the light that may be quantified by imaging in either the visual or non-visual spectrum, such as, for example and without limitation light intensity or color. According to one embodiment, the image is a grayscale image of the well and the aspect of light in the well is gray level. The image may be taken by any suitable imaging device, such as a flat bed optical scanner, an optical plate reader or a top-illumination scanner. Because the methods do not require a microscopic image, the image is taken with an imaging device (camera) that either does not magnify the image optically or the optical magnification is low, such as less than 40× or from 0.5× to 4×.

The methods and, independently, steps thereof, where possible, are typically computer-implemented, that is by software (executable code) processed by a processor. According to one method, an area under the curve (AUC) is calculated for the profile when the volume of the volume of liquid in the meniscus is calculated. In one embodiment, the profile is taken across the meniscus on a line extending perpendicular from the wall. The methods may employ a device comprising two or more discrete cell cultures at independently addressable physical locations, such as an array or multi-well dishes, for example as are known in the art and are commercially available. In a multiwell device, the cells are cultured on one or more membranes of a cell culture device with two or more wells, each well independently comprising a membrane and a wall about a perimeter of the membrane and each membrane contacting cell culture medium on a side opposite the cells. To facilitate comparison between two sample cultures, cells can be cultured on two or more membranes in two or more wells of the device and the two or more wells are imaged at the same time and volumes of liquid in each of the two or more wells is determined and output for each of the two or more wells according to steps (d)-(f). For example a test sample is placed in one well and a second well can be used as a control. According to one embodiment, for example useful in cystic fibrosis—related assays, the cells are bronchial airway cells.

According to an alternate embodiment, the methods further include adding an optically-active composition to the ASL liquid prior to imaging. The optically-active compositions affect some optical property of the ASL such that the meniscus can be imaged in a manner that permits quantification of the meniscus volume according to methods described herein. Suitable optically-active compositions include, without limitation: particles that suspend in the ASL that affect the passage of light through the ALS in a detectable manner, including opaque particles or light-scattering particles such as gold particles, latex particles, polymeric particles, emulsions, etc.; non-absorbable dyes or fluorescent compositions, such as non-absorbable fluorescently labeled dextran. Additional optically-active compositions useful in the described methods would be readily recognized by a person of ordinary skill in the art. Dyes can be imaged either by overall transparency or transparency to specific wavelengths of light and fluorescent compositions can be measured by illuminating the wells with light (e.g., UV light) at an appropriate excitation wavelength for the fluorescent composition and imaging at an emission wavelength of the fluorescent composition.

Also provided is a system for implementing the methods described above in any of the described embodiments. The system comprises an imaging device; and a computer connected to the imaging device comprising a processor and executable instructions for quantifying surface hydration in an air-liquid culture of epithelial cells on a membrane from an image of an air-liquid culture on a membrane in a well, the well comprising a wall about a perimeter of the well, in which the image is generated by illuminating the well in a manner such that a volume of a meniscus of liquid on the cells, if present, can be determined from an aspect of light in the well, the executable instructions, when processed by the computer: producing a profile of the one aspect of light in an area of the well adjacent to the wall and extending past a portion of the wall in which a meniscus forms when a liquid is present on the cells; calculating a volume of liquid in the meniscus using the profile of the aspect of light as representative of a total volume of liquid present on the cells, thereby determining a measurement of the volume of liquid on the cultured epithelial cells in the well; and producing an output from calculating step (ii) of the volume of liquid on the cultured epithelial cells in the well. The imaging device comprises a light source and a sensor for recording an image of the well(s). As above, the light for illuminating the wells may be transmitted light that is passed through the cell culture or illumination from the same side as the imaging device, and may be coherent (e.g., laser), or non-coherent (e.g., a light bulb) and any suitable wavelength. The sensor may be any form of image sensor, such as CCD- or CMOS-type image or video sensors.

According to any embodiment described herein, one non-limiting embodiment of a computer script useful in calculating liquid volume performs the following:
 i. iterates though each well on the plate individually;
 ii. finds the center of each individual culture;
 iii. measures the light/florescent intensity radially from the center of the well to the edge of the cell culture in 360 degrees;
 iv. fits the intensity profile to a sigmoidal equation to derive several mathematic variables which describe the meniscus (EC50, Max light intensity, minimum light intensity, area under the curve, meniscus length); and
 v. derives the liquid volume using an experimentally derived meniscus/volume standard curve.

Although this is one computer-implemented method of determining cell volume, other methods may be apparent to those of ordinary skill in the art.

While the Example below is specifically directed to screening therapies for cystic fibrosis, it is envisioned that the present invention is readily adapted for other applications.

Example 1

Primary Human Airway Epithelial Cell Culture.

HBE cells were cultured from excess pathological tissue following lung transplantation and organ donation under protocols approved by the Universities of Pittsburgh and North Carolina Investigational Review Boards. Cells were studied following 3-6 weeks of culture and considered differentiated when a mucociliary phenotype was apparent on phase contrast microscopy.

Confocal Measurement of ASL Height and ASL Volume.

Human bronchial epithelial cultures were grown under air-liquid conditions on 12 mm diameter Transwell clear membranes (Corning) until fully differentiated as previously described. Immediately prior to measuring the ASL, cultures were washed 3 times with PBS to remove excess mucus. 2 mg/ml Rhodamine-dextran (10 kD) was added to the final wash and the PBS was aspirated with a Pasteur pipette until ASL height was at minimal levels. Cultures were then placed in a chamber on the stage of an inverted Lecia SP5 confocal microscope. ASL height was then measured using a 63×1.2 NA glycerol immersion lens as previously described. To obtain images of the ASL meniscus, cultures were scanned in XZ-mode using a 20×, 0.7 NA or a 10×, 0.4 NA dry, objective lens. The cross-sectional image of the meniscus was obtained from 4 different regions at the perimeter of the culture (corresponding to 0°, 90°, 180° and 270°). The cross-sectional surface area of each meniscus was measured using ImageJ. Since the confocal microscope laser beam intensity diminishes with distances >~30 μm in fluid, the laser power and gain were increased to the point that the region of the ASL image nearest the laser beam was saturating in order to visualize the portion of the meniscus at the air-liquid interface. However, since the meniscus follows a uniform path, when the regions of interest were drawn, obvious image blurring and saturation were ignored.

Figure 1F:
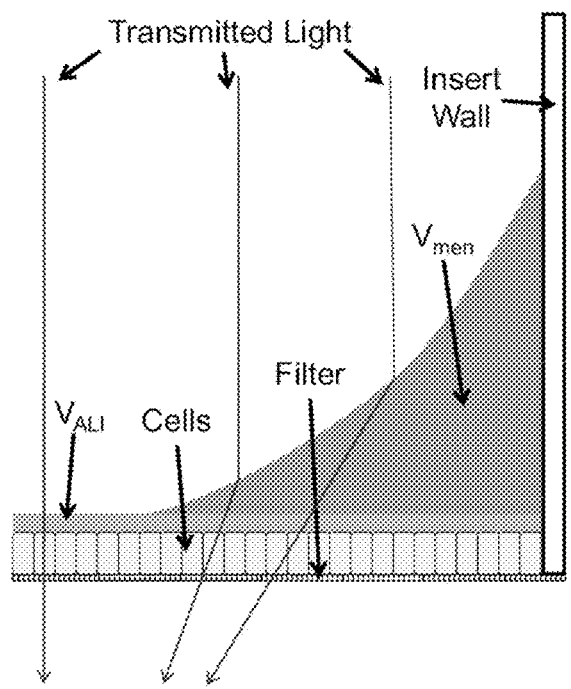
FIG. 1F is a schematic demonstrating the shape of the meniscus from an XZ perspective.

Referring to FIG. 1F, to obtain the meniscus volume ($V_{men}$) the meniscus was assumed to be cylindrically symmetric. Thus, $V_{men}$ was calculated by multiplying the average of the four cross-sectional surface areas of the meniscus (0°, 90°, 180° and (270°) by the circumference of the meniscus (nd). The remainder of the ASL volume covering the thin film liquid present across the air-liquid interface ($V_{ALI}$) was calculated by multiplying the ASL height by $\pi r^2$, assuming this volume was a cylinder. The total ASL volume was the calculated as the sum of $V_{men}+V_{ALI}$.

Measurement of ASL Volume Using Refracted Light Microscopy.

HBE cultures grown in a twenty four well plate on 0.33 $cm^2$ filter inserts (See, e.g., FIG. 1B) were visualized with a standard cell culture microscope (Olympus CK40) with a 5× plain light objective (Zeiss) and imaged using a Scion CFW 1610M camera with μManager (30). Images of the meniscus were taken at the culture perimeter at 90° or 270° without phase contrast. A custom algorithm was developed using ImageJ to automate the analysis of the meniscus as discussed in the results section.

The Fluid Meniscus Surrounding HBE Cultures Reflects the ASL Volume.

Figure 2A:
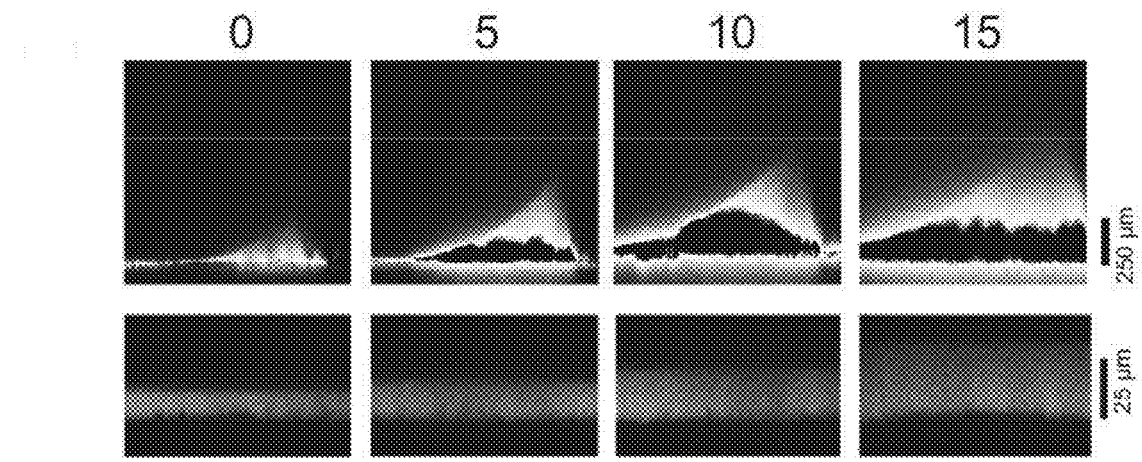
FIG. 2A is a typical images of the ASL meniscus, labeled with rhodamine-dextran, which occurs at the interface between the cell culture periphery and a tissue culture insert wall.

During the initial development of confocal ASL height measurements, the ASL height increment for a given volume of apical fluid was less than predicted. This discrepancy was attributed to accumulation of fluid within a meniscus at the edge between the culture and the Transwell wall. However, the partitioning of the ASL between the meniscus and the thin film ASL were not elucidated. Therefore, a method was developed to image the ASL height across a large surface area which allows for calculation of the ASL volume contained both within the fluid meniscus ($V_{men}$) and across the surface of the HBE culture grown on the air-liquid interface ($V_{ALI}$). Accumulated mucus was removed by several washes with PBS and the ASL labeled with Rhodamine-dextran. The apical surface was subsequently aspirated to set the ASL height at minimal levels. As shown in the low magnification images of the meniscus and in the higher magnification thin film images of ASL height in FIG. 2A (top panel and bottom panel respectively), a small volume of fluid remains following aspiration. From these images, the $V_{men}$ was calculated to be 2.1±0.3 µL, compared to 1.5±0.2 µL in the $V_{ALI}$. Therefore, 3.6±0.2 µL of ASL remained present on the apical surface of 12 mm HBE cultures following aspiration, which is likely the result of a small residual volume that cannot be aspirated from the apical surface following labeling with the fluorescent fluid.

Figure 2B:
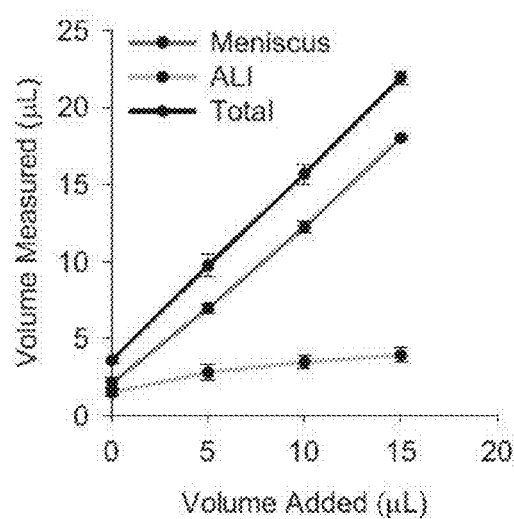
FIG. 2B is a mean calculated ASL volume after sequential 5 µl additions of PBS to the mucosal surface. During this experiment, all PBS contained 100 µM amiloride to block Na and fluid absorption. Data shown are mean $V_{men}$ (meniscus), $V_{ALI}$ (ALI), and total ASL volume (n=3 cultures).

Next, the distribution patterns of the ASL were determined as the volume was experimentally expanded. As shown in FIG. 2B, the $V_{men}$ and $V_{ALI}$ (See, FIG. 1F) were measured following the serial addition of 5 µL boluses of PBS. There was excellent correlation with the total measured ASL volume and the actual volume added plus the residual volume that could not be aspirated ($R^2$=0.98, slope=1.2±0.04, y intercept=3.6±0.4). During the titration, $V_{ALI}$ doubled; but as clearly seen in FIG. 2B, the bulk of the volume added went to the meniscus and little went into $V_{ALI}$. This behavior is consistent with the contact angle of the meniscus being zero at the interface with the thin film ASL and nonzero at the interface with the culture insert wall which is made of polystyrene and therefore somewhat hydrophobic. As the ASL volume increased, the meniscus between these two surfaces enlarged; extending both across the thin film ASL and up the side wall, an action which would continue until the menisci from diametrically opposed positions on the insert meet. Presumably, at this point, any additional fluid would raise the height of the ASL in the center of the cell.

Figure 2C:
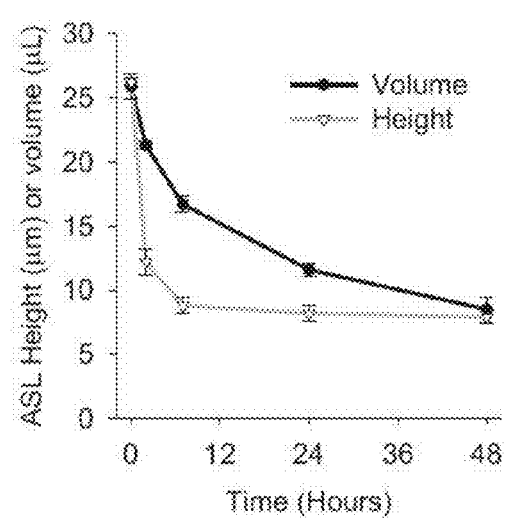
FIG. 2C is a mean ASL height and ASL volume after the apical addition of 15 µl PBS. Data shown are mean ASL height or volume (n=6 cultures).

The kinetics of ASL volume absorption and ASL height regulation following an apical fluid challenge were then compared. As shown in FIG. 2C, 15 µL of fluorescently labeled PBS was applied to the apical surface of differentiated HBE cultures and the height of the thin film ASL on the HBE cells and the total ASL volume were serially measured over a 48 hour period. The thin film ASL height rapidly returned to a basal height of ~10 µm, suggesting that the ASL height is acutely regulated by HBE cultures. Conversely, the ASL volume required a longer period of time to return to basal levels, due to the accumulation of fluid in the meniscus. These results suggest that the ASL height in close proximity to the cells and the total ASL volume are differentially regulated; whereas the thin film ASL height is acutely determined by active ion transport, the ASL volume present in the meniscus appears to serves as a reservoir compartment that requires an extended period of time to return to basal levels.

Development of a Simple Method to Measure the ASL Volume.

Because the bulk of the total ASL volume is present within the meniscus surrounding the HBE culture insert, a simple method of assessing the ASL volume by imaging the meniscus was developed. When examined with a standard cell culture microscope under low power, the fluid meniscus appears as a gradation of grey scales that are generated by the refraction of light as it passes though the sloping liquid layer, diagramed schematically in FIG. 1F. In the representative photomicrograph in FIG. 3A, the wall of the culture insert is oriented to the right side of the image. Adjacent to the wall, the dark meniscus begins and gradually fades as the liquid meniscus ends on the flat thin film ASL. An image of the meniscus is generated by the refraction of the light at the meniscus interface away from the incident direction and the collection objective. The greater the angle of the air/liquid interface, the greater the angle of refracted light, and the darker the image. Therefore, the image of the meniscus is determined by the shape of the meniscus and as such reflects the volume and surface tension of the ASL contained within the culture insert.

Figure 3A:
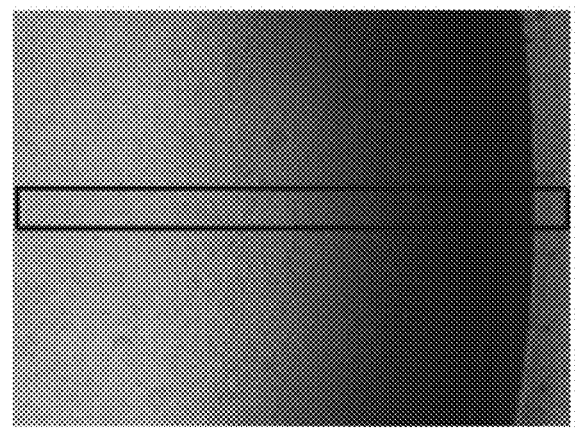
FIG. 3A is a representative photomicrograph imaged with a 5× objective demonstrating a Transwell insert wall (right) adjacent to a fluid meniscus that surrounds the HBE culture. The 200-pixel-high region of interest used for the automated analysis is shown by the black box.
Figure 3B:
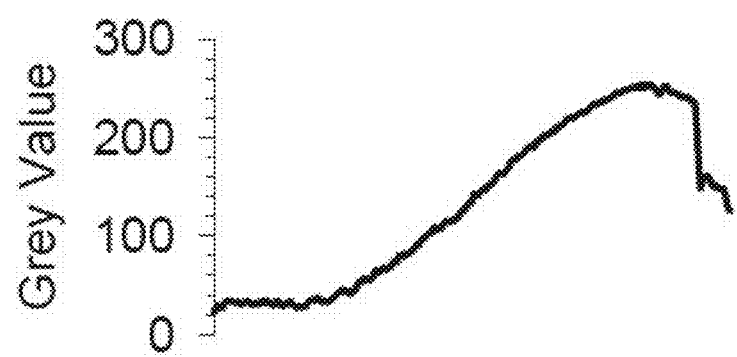
FIG. 3B is a raw light intensity across a meniscus. The intensity array is truncated when the light intensity begins to decline to remove the insert wall from the analysis.
Figure 3C:
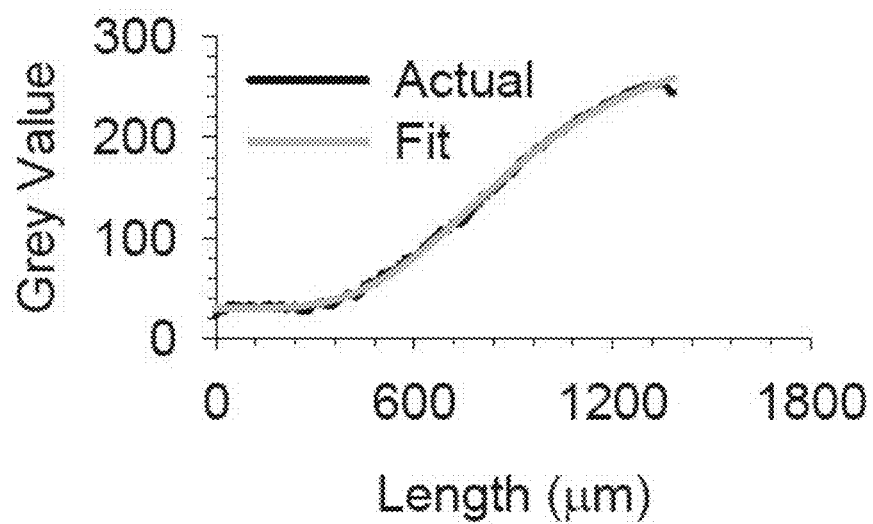
FIG. 3C is a comparison of the actual (actual, black line) intensity profile and the derived (Fit, gray line) intensity profile from the sigmoidal fit.

In order to standardize the quantification of the meniscus image, a custom script using the open-source ImageJ software was developed. To remove noise and obtain a representative profile of the grey levels generated by the meniscus, the gray level is averaged down a line of 200 pixels oriented perpendicular to the radial direction of the cell culture insert. This averaged gray level is then plotted vs the radial distance, as shown in FIGS. 3A-B. The grey level array is then truncated at the point at which the value begins to drop below the peak value, as shown in FIG. 3C (black trace), in order to remove the culture insert wall (see, e.g., FIG. 1F) from the analysis. The truncated array (Grey Value vs length) is then fit to a four parameter logistic function where:

$$\text{Grey Value} = \min + (\max - \min)/(1 + (x/EC50)^{Hillslope}).$$

When fit to this equation, the $R^2$ values are typically greater than 0.99 indicating an excellent fit. The length of the meniscus can be determined as the length from where the grey value is greater than min to the end of the array and the area under the curve (AUC) is measured using the numerically integrated rectangular rule. Therefore, the meniscus length, AUC, and several parameters describing the meniscus shape can be mathematically derived from the image of the meniscus using an automated image analysis algorithm.

Figure 4A:
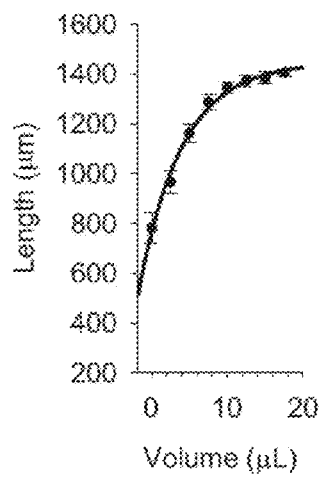
FIG. 4A is a graph of the calibration of an HBE culture meniscus with the ASL volume. The apical surfaces of differentiated HBE cultures were aspirated and subsequently used for volume titrations. Increments of PBS (2.5 µl) were applied to the apical surface and the ASL meniscus was measured. The data shown is the mean (±SEM) meniscus length.
Figure 4B:
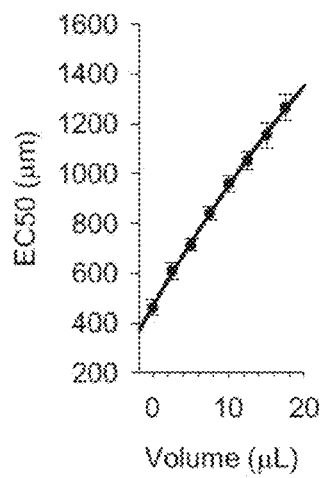
FIG. 4B is a graph of a calibration of the HBE culture meniscus with the ASL volume. The apical surfaces of differentiated HBE cultures were aspirated and subsequently used for volume titrations. Increments of PBS (2.5 µl) were applied to the apical surface and the ASL meniscus was measured. The data shown is the mean distance from the culture insert wall to half of the grey value between max and min (EC50).
Figure 4C:
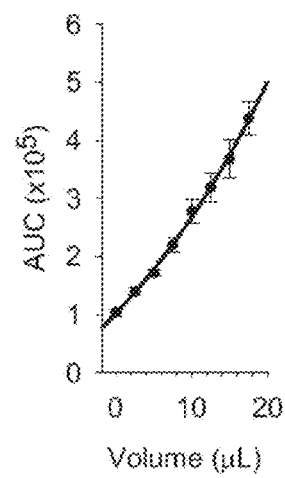
FIG. 4C is a graph of the calibration of the HBE culture meniscus with the ASL volume. The apical surfaces of differentiated HBE cultures were aspirated and subsequently used for volume titrations. Increments of PBS (2.5 µl) were applied to the apical surface and the ASL meniscus was measured. The data shown is the area under the curve (AUC) for the HBE cultures with increasing ASL volume (n=12 cultures from 2 tissue donors).

Due to the complexity of the image formation as the transmitted light passes through both the meniscus and culture insert, the intensity profile is not a simple XZ representation of the meniscus shape. Therefore, the correlation between the derived parameters of the intensity profile and the ASL volume were determined, rather than mathematically calculating the volume based on the AUC of the intensity profile. In order to establish the relationship between the refracted light image of the meniscus and the ASL volume, the native ASL was aspirated from the apical surface of differentiated HBE cultures and the meniscus was imaged following serial additions of 2.5 µL PBS to the apical surface. As shown in FIGS. 4A-C, the meniscus length, EC50, and area under the curve (AUC) demonstrated a dose response to increasing ASL volume. Due to limitations in the field of view and the length of the mensicus, complete visualization of the meniscus with volumes >10 µL proved difficult. Because of the limited field of view, the meniscus length reached a plateau when the ASL volume exceeded 10 µL because the light intensity did not drop below the "min"

parameter from the sigmoidal fit. However, the EC50 and AUC continued to increase with increasing volumes allowing for an ASL volume resolution of approximately 0-20 μL. Because the EC50 measurements correlated well with the ASL volume over a wide range, this value was used to calculate the ASL volume for the remainder of the experiments. Thus, the ASL volume can be measured from the image of the meniscus by integrating the EC50 value with the experimentally derived calibration curve shown in FIG. 4B.

Figure 5A:
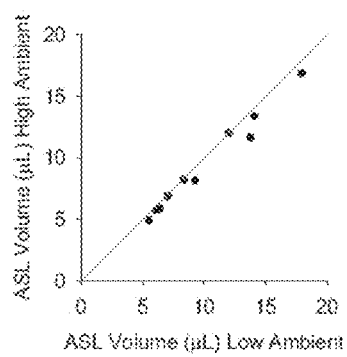
FIG. 5A is a graph of a comparison between low and high ambient light surrounding the microscope.
Figure 5B:
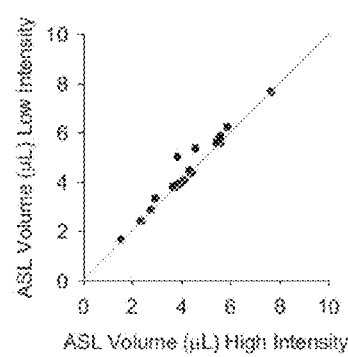
FIG. 5B is a graph of the measured ASL volume with either low or high illumination intensity. This demonstrates the robust nature of the ASL volume measurement.
Figure 5C:
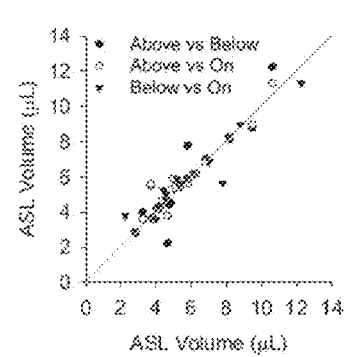
FIG. 5C is a graph of the comparison between fine focus adjusted above, on, or below an HBE culture.

The effect of various potential confounding factors on the ASL volume measurement were examined next. First, it was found that it is advantageous to orient the intensity profile so that it is perpendicular to a tangent of perimeter of the cell culture insert. Therefore, by convention all images of the meniscus were acquired at 90° or 270° with respect to the culture insert allowing for automated analysis. As shown in FIGS. 5A-C, the measured ASL volume for an individual filter was unchanged by the ambient light in the room. Furthermore, the light intensity of the microscope had little effect on the measured ASL volume, provided that the light intensity of the image was not over or under saturated. The ASL volume measurement was not significantly altered by the focal plane at which the images were obtained. The best measurements were obtained when the meniscus was imaged without phase contrast, because the phase contrast introduced ring artifacts. Likewise, the intensity profile quality suffered from noise introduced by the culture insert wall, when the focal plane was above the filter. Based on the robust measurement of the ASL volume, the images can be rapidly obtained with a low NA objective at a focal plane slightly below the filter, without the need for frequent refocusing or adjustment of the light intensity.

HBE Cells Cultured from CF Donors have a Decreased ASL Volume Compared to Non-CF Cells.

Figure 6A:
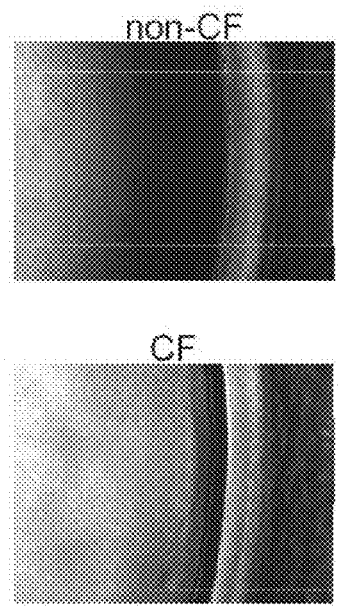
FIG. 6A is a set of representative photomicrographs of meniscus present on CF (top) and non-CF (bottom) HBE cultures.
Figure 6B:
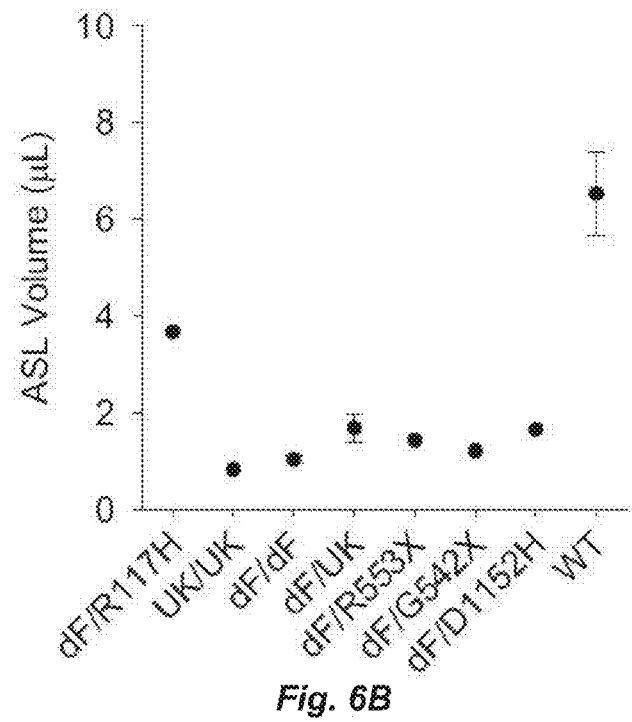
FIG. 6B is a chart of the Mean ASL volume for each tissue donor arranged by CFTR genotype (n=11 CF and 11 non-CF tissue donors).

The lack of functional CFTR in CF lung disease leads to defective fluid secretion and excessive fluid absorption from the luminal airway surface of CF HBE. It was hypothesized that the ASL volume of CF HBE would also be decreased with respect to non-CF tissue. The ASL volumes of HBE cultured from several tissue donors containing a variety of CFTR genotypes were measured under baseline conditions with no prior manipulation to the native ASL, as shown in FIGS. 6A-B. Overall HBE cultured from CF tissue donors had an average ASL volume of 1.5±0.2 μL vs 6.5±0.9 μL in non-CF tissues ($p<0.001$ by Mann-Whitney Rank Sum, n=11 tissue donors). Aside from one donor with a R117H/dF CFTR genotype, HBE cultured from CF donors had less than 2 μL of ASL. Interestingly, the ASL volume of the CF HBE cultures containing one copy of a mild mutation (R117H/dF CFTR) had an intermediate ASL volume between the severe CFTR mutations and WT genotypes. The non-CF HBE cultures had a more variable ASL volume with respect to the uniformly low volume present on the CF cultures. Therefore, CF HBE cultures have a reduced ASL volume and the refracted light from the meniscus method of measuring the volume is sensitive enough to detect this disease relevant difference.

ASL Volume Response to Apical Tonicity and Ion Channel Blockers.

Figure 7:
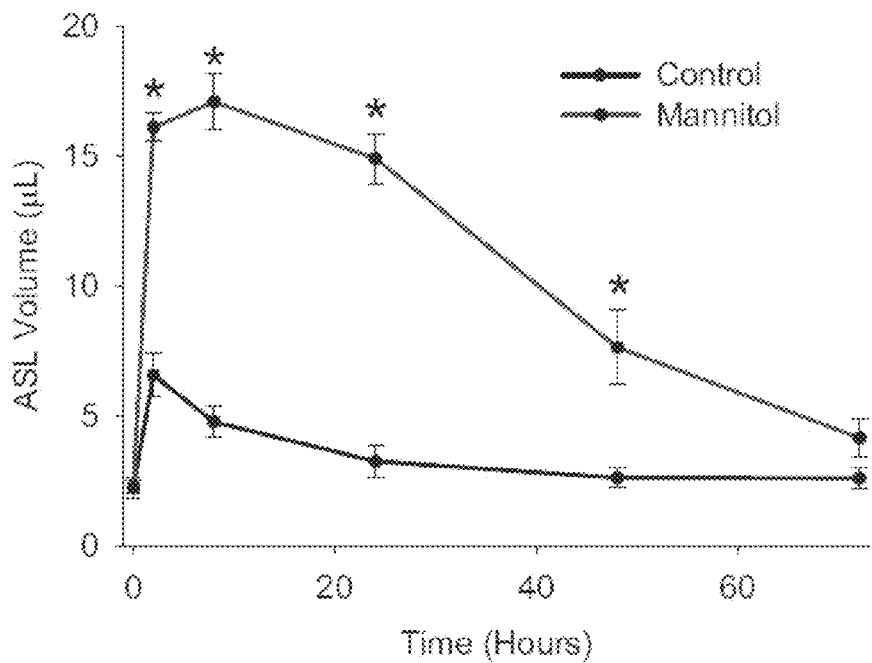
FIG. 7 is a graph of a Comparison of the ASL volume after expansion with isotonic versus hypertonic fluid. The ASL volume of differentiated HBE cultures was measured at 0, 2, 4, 8, and 24 hours after ASL volume expansion with Ringer's solution with or without 300 mM mannitol. Data shown are mean ASL volume (±SEM) (n=18 cultures from 3 different tissue donors).

To define the strengths and limitations of the ASL volume method of assessing the airway surface hydration status, the ASL volume response to manipulations with predictable effects was examined. First the effect of hypertonicity on CF HBE cultures was examined. The ASL volume of differentiated CF HBE cells was expanded with 5 μL PBS±300 mM mannitol and the ASL volume was measured at 0, 4, 8, 24, 48, and 72 hours following the fluid bolus. As shown in FIG. 7, the cultures that were treated with the hypertonic fluid had a more pronounced and prolonged ASL volume expansion compared to the filters exposed to isotonic fluid. Therefore, using this simple method of assessing the ASL volume we are able to measure changes in the ASL volume in response to apical fluid boluses and obtain the predicted response to hypertonic fluids.

Figure 8A:
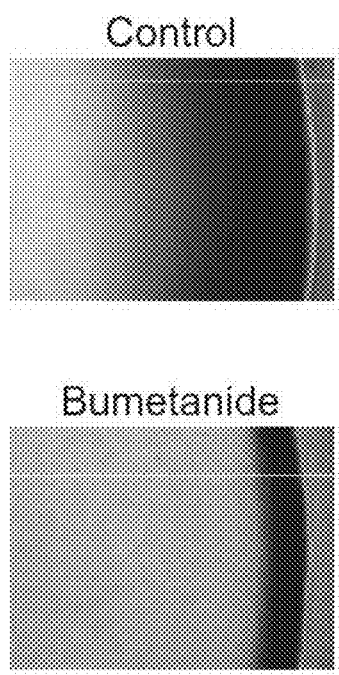
FIG. 8A is a set of representative photomicrograph of the meniscus under control and bumetanide-treated conditions.
Figure 8B:
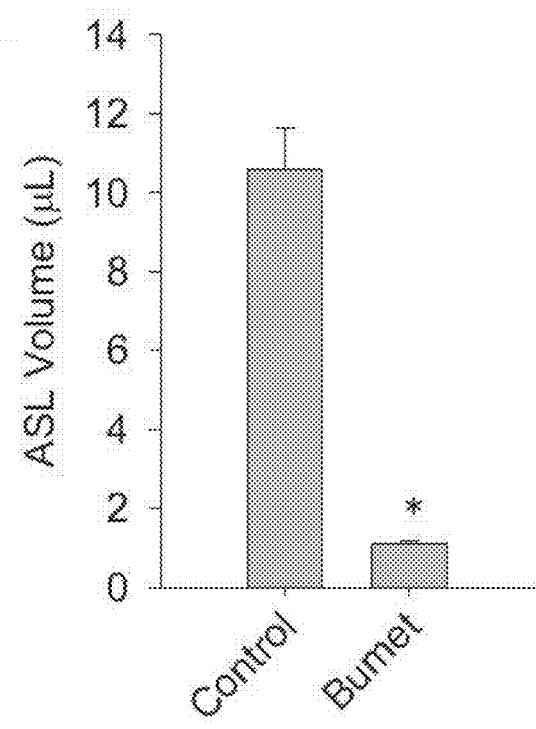
FIG. 8B is a chart of the Mean (±SEM) ASL volume of HBE cultures with or without 100 µM bumetanide (n=16 cultures from 3 tissue donors). *P<0.001 ASL height is different from control.

Next it was determined whether changes in the ASL volume in response to inhibition of the basolateral sodium potassium chloride co-transporter with bumetanide could be measured. Because this drug would be expected to block active chloride secretion from HBE cultures, it was hypothesized that the ASL volume would be decreased following treatment with bumetanide. Differentiated HBE cultures were cultured in the presence or absence of 100 μM bumetanide for three days prior to measuring the ASL volume. As shown in FIGS. 8A-B, the ASL volume decreased to 1.1±0.1 μL in the bumetanide treated cultures, compared to 10.6±1.0 μL in the control filters ($p<0.001$, n=15 cultures derived from 3 different tissue donors). These results confirm that ASL volume is actively regulated and dependent on $Cl^-$ secretion.

Example 2

A computer script was prepared in the open-source ImageJ software that is useful in calculating liquid volume using an image of one or more wells according to any of the methods described herein. The script performs the following steps:
i. iterates though each well on the plate individually;
ii. finds the center of each individual culture;
iii. measures the light/florescent intensity radially from the center of the well to the edge of the cell culture in 360 degrees;
iv. fits the intensity profile to a sigmoidal equation to derive several mathematic variables which describe the meniscus (EC50, Max light intensity, minimum light intensity, area under the curve, meniscus length); and
v. derives the liquid volume using an experimentally derived meniscus/volume standard curve.

While the present invention is described with reference to several distinct embodiments, those skilled in the art may make modifications and alterations without departing from the scope and spirit. Accordingly, the above detailed description is intended to be illustrative rather than restrictive.

I claim:
1. A method of quantifying surface hydration in an air-liquid culture of epithelial cells, the method comprising:
illuminating at least one well containing the culture of epithelial cells, the at least one well having a membrane and a wall about a perimeter of the membrane, in a manner such that a volume of a meniscus of liquid on the epithelial cells, if present, can be determined from an aspect of light in the at least one well;
imaging an entire surface of the membrane and the wall with an imaging device to produce an image of the at least one well;
producing from the image, using a computer-implemented method, a plurality of profiles of the aspect of light in a direction extending radially from a central point of the at least one well;
calculating, using a computer-implemented method, a volume of liquid in the meniscus of the at least one well using the plurality of profiles of the aspect of light as representative of a total volume of liquid present on the epithelial cells, thereby determining a measurement of the volume of liquid on the epithelial cells; and providing an output of the calculated volume of liquid on the epithelial cells.

2. The method of claim 1, in which the at least one well is illuminated by light from an opposite side of the membrane from the imaging device such that light is refracted differently at a meniscus adjacent the wall as compared to a point on the membrane where no meniscus forms.

3. The method of claim 2, in which the light is an unfocused, transmitted light.

4. The method of claim 1, in which the aspect of light in the at least one well is light intensity.

5. The method of claim 1, in which the image is a grayscale image of the at least one well and the aspect of light is gray level.

6. The method of claim 1, wherein the imaging device is one of a flat bed optical scanner, an optical plate reader, or a top-illumination scanner.

7. The method of claim 1, wherein the at least one well is imaged at an optical magnification of less than 40×.

8. The method of claim 1, wherein the at least one well is imaged at an optical magnification of 0.5× to 4×.

9. The method of claim 1, wherein the at least one well is not optically magnified when imaged.

10. The method of claim 1, in which an area under the curve (AUC) is calculated for the plurality of profiles when the volume of liquid in the meniscus of the at least one well is calculated.

11. The method of claim 1, in which the epithelial cells are bronchial airway cells.

12. The method of claim 1, in which the plurality of profiles of the aspect of light are taken across the meniscus on a line extending perpendicular from the wall to the central point of the at least one well.

13. The method of claim 1, further comprising, adding an optically-active composition to the epithelial cells prior to illuminating the plurality of wells.

14. A method of quantifying surface hydration in an air-liquid culture of epithelial cells, the method comprising:
adding an optically-active composition to at least one well containing the culture of epithelial cells, the at least one well having a membrane and a wall about a perimeter of the membrane;
illuminating the at least one well at an excitation wavelength to activate the optically-active composition such that a volume of a meniscus of liquid on the epithelial cells, if present, can be determined from an aspect of light in the at least one well;
imaging an entire surface of the membrane and the wall with an imaging device at an emission wavelength of the optically-active composition to produce an image of the at least one well;
producing from the image, using a computer-implemented method, a plurality of profiles of the aspect of light in a direction extending radially from a central point of the at least one well;
calculating, using a computer-implemented method, a volume of liquid in the meniscus of the at least one well using the plurality of profiles of the aspect of light as representative of a total volume of liquid present on the epithelial cells, thereby determining a measurement of the volume of liquid on the epithelial cells; and
providing an output of the calculated volume of liquid on the epithelial cells.

15. The method of claim 14, wherein the optically-active composition is a fluorescent composition.

16. A system for quantifying surface hydration in an air-liquid culture of epithelial cells, comprising:
an imaging device; and
a computer connected to the imaging device comprising a processor and executable instructions for quantifying surface hydration in the epithelial cells from an image of at least one well containing the epithelial cells, the at least one well having a membrane and a wall about a perimeter of the membrane, in which the image is generated by illuminating the at least one well in a manner such that a volume of a meniscus of liquid on the epithelial cells, if present, can be determined from an aspect of light in the at least one well, the executable instructions, when processed by the computer, comprising:
obtaining an image using the imaging device of an entire surface of the membrane and the wall of the at least one well;
producing from the image, using a computer-implemented method, a plurality of profiles of the aspect of light in a direction extending radially from a central point of the at least one well;
calculating a volume of liquid in the meniscus using the plurality of profiles of the aspect of light as representative of a total volume of liquid present on the epithelial cells, thereby determining a measurement of the volume of liquid on the epithelial cells; and
providing an output of the calculated volume of liquid on the epithelial cells.

17. The system of claim 16, in which the imaging device is one of a flat bed optical scanner, an optical plate reader or a top-illumination scanner.

18. The system of claim 16, in which the at least one well is illuminated by light from an opposite side of the membrane from the imaging device such that light is refracted differently at a meniscus adjacent the wall as compared to a point on the membrane where no meniscus forms.

19. The system of claim 16, in which the aspect of light in the at least one well is light intensity.

20. The system of claim 16, in which the plurality of profiles of the aspect of light are taken across the meniscus on a line extending perpendicular from the wall to the central point of the at least one well.

* * * * *

UNITED STATES PATENT AND TRADEMARK OFFICE
CERTIFICATE OF CORRECTION

PATENT NO. : 9,784,725 B2
APPLICATION NO. : 15/157475
DATED : October 10, 2017
INVENTOR(S) : Michael Myerburg Page 1 of 1

It is certified that error appears in the above-identified patent and that said Letters Patent is hereby corrected as shown below:

On the Title Page

Column 1, Before Item (51) insert -- Related U.S. Application Data, item (63) Continuation of application No. 13/650,198, filed on Oct. 12, 2012, now Pat. No. 9,360,414. Item (60) Provisional application No. 61/547,106, filed on Oct. 14, 2011. --

Column 2, Item (57) ABSTRACT, Line 2, delete "though" and insert -- through --

Signed and Sealed this
Twenty-second Day of May, 2018

Andrei Iancu
*Director of the United States Patent and Trademark Office*